(12) United States Patent
Bolduc

(10) Patent No.: US 7,959,670 B2
(45) Date of Patent: Jun. 14, 2011

(54) CATHETER-BASED FASTENER IMPLANTATION METHODS

(75) Inventor: Lee Bolduc, Sunnyvale, CA (US)

(73) Assignee: Aptus Endosystems, Inc., Sunnyvale, CA (US)

( * ) Notice: Subject to any disclaimer, the term of this patent is extended or adjusted under 35 U.S.C. 154(b) by 0 days.

(21) Appl. No.: 11/580,584

(22) Filed: Oct. 13, 2006

(65) Prior Publication Data
US 2007/0032863 A1  Feb. 8, 2007

Related U.S. Application Data

(60) Division of application No. 10/692,282, filed on Oct. 23, 2003, now Pat. No. 7,128,754, which is a continuation-in-part of application No. 10/307,226, filed on Nov. 29, 2002, which is a continuation-in-part of application No. 10/271,334, filed on Oct. 15, 2002, now Pat. No. 6,960,217.

(60) Provisional application No. 60/333,937, filed on Nov. 28, 2001.

(51) Int. Cl.
*A61F 2/06* (2006.01)

(52) U.S. Cl. ........................ 623/1.36; 606/108; 623/1.24

(58) Field of Classification Search ................ 623/1.14, 623/1.36, 2.17, 2.18; 606/108; *A61F 02/06*
See application file for complete search history.

(56) References Cited

U.S. PATENT DOCUMENTS

| | | | |
|---|---|---|---|
| 5,676,696 A | 10/1997 | Marcade | |
| 6,074,418 A | 6/2000 | Buchanan et al. | |
| 6,409,757 B1 | 6/2002 | Trout, III et al. | |
| 6,702,844 B1 * | 3/2004 | Lazarus | 623/1.14 |
| 6,986,784 B1 * | 1/2006 | Weiser et al. | 623/1.1 |
| 2004/0039405 A1 * | 2/2004 | Petrovic et al. | 606/155 |
| 2005/0038506 A1 * | 2/2005 | Webler et al. | 623/2.11 |
| 2005/0043790 A1 * | 2/2005 | Seguin | 623/2.18 |

FOREIGN PATENT DOCUMENTS

| | | |
|---|---|---|
| EP | 0663184 | 7/1995 |
| WO | WO99/33402 | 7/1999 |

OTHER PUBLICATIONS

Office Action; U.S. Appl. No. 10/692,282; Applicant: Lee Bolduc; Date: 30 Aug. 30, 2005; pp. 5.
Response to Office Action; Amendment B; U.S. Appl. No: 10/692,282; Applicant: Lee Bolduc; Date: Feb. 28, 2006; pp. 5.
Notice of Allowance; U.S. Appl. No. 10/692,282; Applicant: Lee Bolduc; Date Jun. 13, 2006; pp. 3.

* cited by examiner

*Primary Examiner* — Corrine M McDermott
*Assistant Examiner* — Jason-Dennis Stewart
(74) *Attorney, Agent, or Firm* — Morrison & Foerster LLP

(57) ABSTRACT

Methods implant one or more fastening structure(s) in a targeted body region, e.g., within a hollow body organ or an intraluminal space. The fastening structure(s) are implanted to a vessel wall, and serve to secure a prosthesis within the hollow body organ or intraluminal space.

7 Claims, 18 Drawing Sheets

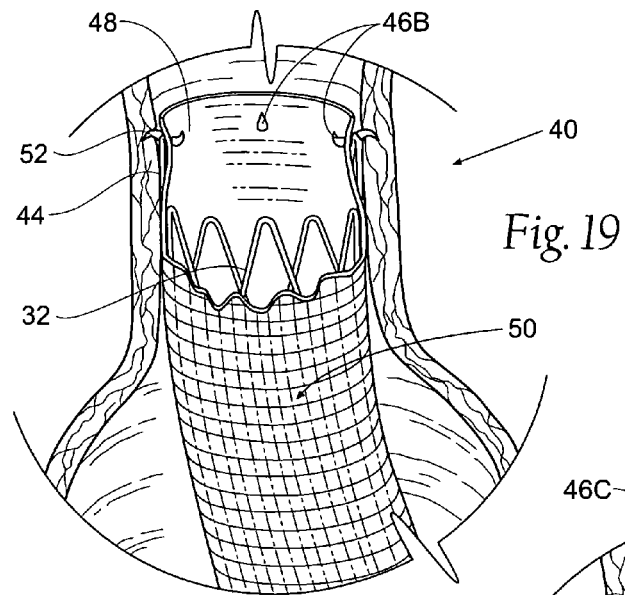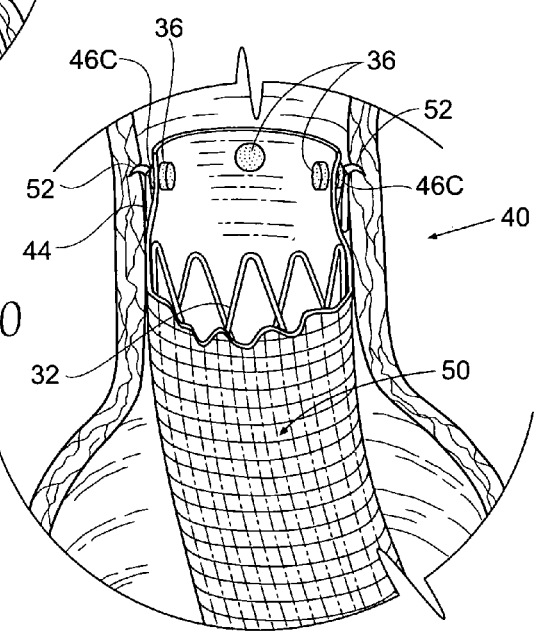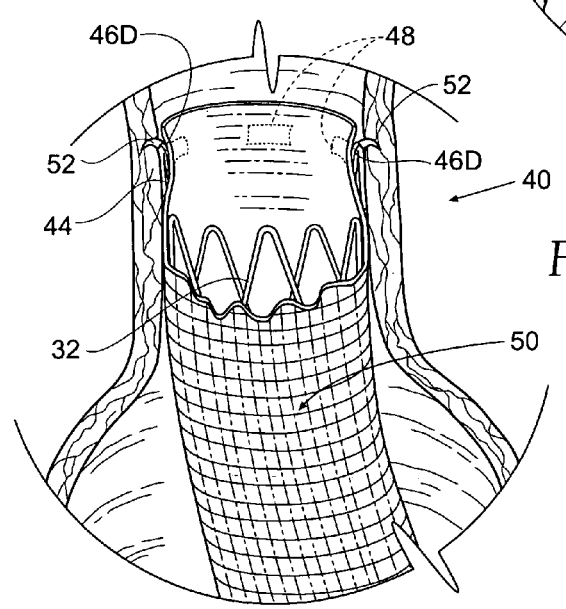

CATHETER-BASED FASTENER IMPLANTATION METHODS

RELATED APPLICATIONS

This application is a division of U.S. patent application Ser. No. 10/692,282, filed Oct. 23, 2003, now U.S. Pat. No. 7,128,754 and entitled "Catheter-Based Fastener Implantation Apparatus and Method," which is a continuation-in-part of U.S. patent application Ser. No. 10/307,226, filed Nov. 29, 2002, and which is also a continuation-in-part of U.S. patent application Ser. No. 10/271,334, filed Oct. 15, 2002, now U.S. Pat. No. 6,960,217 which claims the benefit of U.S. Provisional Application Ser. No. 60/333,937 filed Nov. 28, 2001 (Expired).

FIELD OF THE INVENTION

The invention relates generally to the delivery of a prosthesis to a targeted site within the body, e.g., for the repair of diseased and/or damaged sections of a hollow body organ and/or blood vessel.

BACKGROUND OF THE INVENTION

The weakening of a vessel wall from damage or disease can lead to vessel dilatation and the formation of an aneurysm. Left untreated, an aneurysm can grow in size and may eventually rupture.

For example, aneurysms of the aorta primarily occur in abdominal region, usually in the infrarenal area between the renal arteries and the aortic bifurcation. Aneurysms can also occur in the thoracic region between the aortic arch and renal arteries. The rupture of an aortic aneurysm results in massive hemorrhaging and has a high rate of mortality.

Open surgical replacement of a diseased or damaged section of vessel can eliminate the risk of vessel rupture. In this procedure, the diseased or damaged section of vessel is removed and a prosthetic graft, made either in a straight or bifurcated configuration, is installed and then permanently attached and sealed to the ends of the native vessel by suture. The prosthetic grafts for these procedures are usually unsupported woven tubes and are typically made from polyester, ePTFE or other suitable materials. The grafts are longitudinally unsupported so they can accommodate changes in the morphology of the aneurysm and native vessel. However, these procedures require a large surgical incision and have a high rate of morbidity and mortality. In addition, many patients are unsuitable for this type of major surgery due to other co-morbidities.

Endovascular aneurysm repair has been introduced to overcome the problems associated with open surgical repair. The aneurysm is bridged with a vascular prosthesis, which is placed intraluminally. Typically these prosthetic grafts for aortic aneurysms are delivered collapsed on a catheter through the femoral artery. These grafts are usually designed with a fabric material attached to a metallic scaffolding (stent) structure, which expands or is expanded to contact the internal diameter of the vessel. Unlike open surgical aneurysm repair, intraluminally deployed grafts are not sutured to the native vessel, but rely on either barbs extending from the stent, which penetrate into the native vessel during deployment, or the radial expansion force of the stent itself is utilized to hold the graft in position. These graft attachment means do not provide the same level of attachment when compared to suture and can damage the native vessel upon deployment.

SUMMARY OF THE INVENTION

The invention provides systems and methods that implant one or more fastening structure(s) in a targeted body region, e.g., within a hollow body organ or an intraluminal space. The fastening structure(s) are implanted to a vessel wall, and serve to secure a prosthesis within the hollow body organ or intraluminal space.

One aspect of the invention provides methods for securing a prosthesis to tissue in a targeted tissue region. The methods (i) introduce at least one fastener into the targeted tissue region; (ii) implant the fastener in tissue in the targeted tissue region; (iii) after (i) and (ii), introduce a prosthesis into the targeted tissue region, and (iv) attach the prosthesis to the fastener to secure the prosthesis to tissue in the targeted tissue region.

Another aspect of the invention provides methods for securing a prosthesis to tissue in a targeted tissue region. The methods (i) introduce a prosthesis into the targeted tissue region; (ii) place the prosthesis into contact with tissue in the targeted tissue region; (iii) after (i) and (ii), introduce at least one stent ring into the targeted tissue region; and (iv) press an outer surface of the stent ring against the prosthesis to secure the prosthesis to tissue within the targeted tissue region.

BRIEF DESCRIPTION OF THE DRAWINGS

The invention will be understood from the following detailed description of preferred embodiments, taken in conjunction with the accompanying drawings, wherein:

FIG. 19 shows a prosthesis that has been mechanically coupled to a stent ring implanted in a vessel wall or hollow body organ, which is illustrative of one embodiment of the systems and methods of the type shown in FIGS. 11 to 15.

FIG. 20 shows a prosthesis that has been magnetically coupled to a stent ring implanted in a vessel wall or hollow body organ, which is illustrative of another embodiment of the systems and methods of the type shown in FIGS. 11 to 15.

FIG. 21 shows a prosthesis that has been chemically coupled to a stent ring implanted in a vessel wall or hollow body organ, which is illustrative of another embodiment of the systems and methods of the type shown in FIGS. 1 to 5.

DETAILED DESCRIPTION OF THE INVENTION

The figures depict various systems and methods 22, 40, and 60 for attaching a prosthesis to a vessel wall or hollow body organ. The systems and methods 22, 40, and 60 can be used anywhere in the body. The systems and methods 22, 40, and 60 lend themselves well to the repair of diseased or damaged sections of a blood vessel, particularly in the repair an abdominal aortic aneurysm. For this reason, the systems and methods 22, 40, and 60 will be described in the context of this indication. Still, it should be recognized that the systems and methods 22, 40, and 60 can be used in other diverse indications.

The figures depict, for purposes of illustration, three general types of systems and methods 22, 40, and 60. These will be called, respectively, Type I (FIGS. 1 to 10), Type II (FIGS. 11 to 21), and Type III (FIGS. 22 to 25).

The three Types I, II, and III share several common features. For example, for all Types I, II, and III, the systems and methods 22, 40, and 60 implant one or more fastening structure(s) in a targeted body region, e.g., within a hollow body organ or an intraluminal space. The systems and methods 22, 40, and 60 can deploy the fastening structure(s) through the vasculature by manipulation from outside the body. The fastening structure(s) are implanted to a vessel wall, and serve to secure a prosthesis within the hollow body organ or intraluminal space. The prosthesis can comprise, e.g., an endovascular graft, which can be deployed without damaging the native blood vessel in either an arterial or a venous system. The endovascular graft can comprise, e.g., a radially expanding vascular stent and/or a stent-graft. The graft can be placed in the vasculature, e.g., to exclude or bridge an aneurysm, for example, an abdominal aortic aneurysm. The graft desirably adapts to changes in aneurysm morphology and repairs the endovascular aneurysm.

The systems and methods 22, 40, and 60 of Types I, II, and III differ in structural details and, sometimes, in the sequence in which the fastening structure(s) and prosthesis are deployed. Each Type I, II, and III will now be described in greater detail.

I. Type I Systems and Methods

Figure 1:
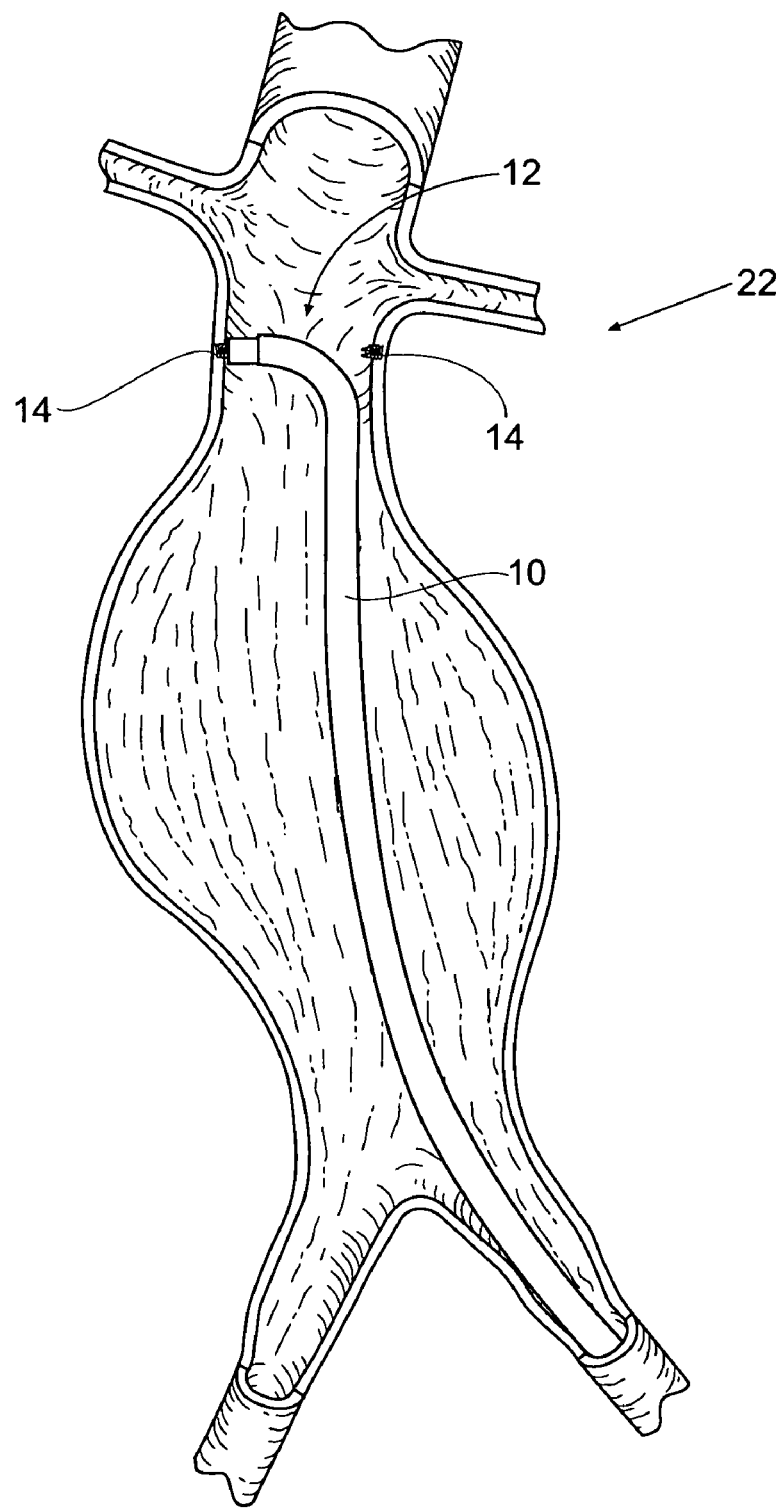
FIGS. 1 to 5 show one type of a system and method for attaching a prosthesis to a vessel wall or hollow body organ, in which the prosthesis is coupled to fasteners, which are implanted prior to deployment of the prosthesis.

FIGS. 1 to 10 depict the systems and methods 22 that can be characterized as a Type I arrangement. In this embodiment, the systems and methods 22 first deploy one or more individual fasteners 14 using a fastener attachment assembly 10. As shown in FIG. 1, the assembly 10 is deployed to a targeted prosthesis attachment site 12. In FIG. 1, the targeted site 12 is shown as being within an abdominal aortic aneurysm. The targeted site 12 can, or course, be elsewhere in the body.

Figure 2:
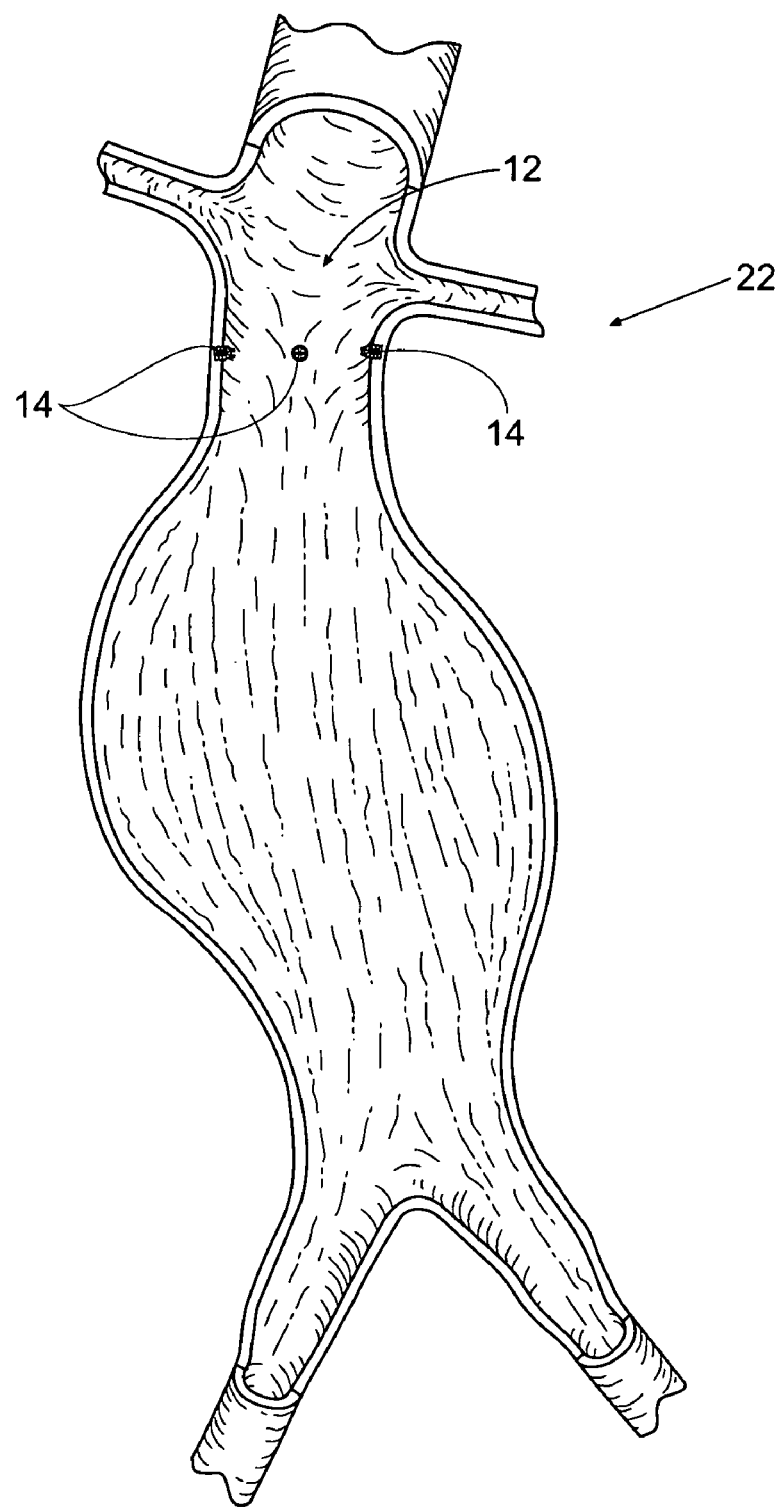

As FIG. 2 shows, the fastener attachment assembly 10 serves the function of implanted one or more fasteners 14 in a desired array in the vessel wall at the targeted site 12 prior to deployment of a prosthesis 20. As will be described in greater detail, the fasteners 14 each includes an attachment element 16 that, in use, couples to a corresponding attachment element 18 on a prosthesis 20 deployed in the site 12.

Figure 3:
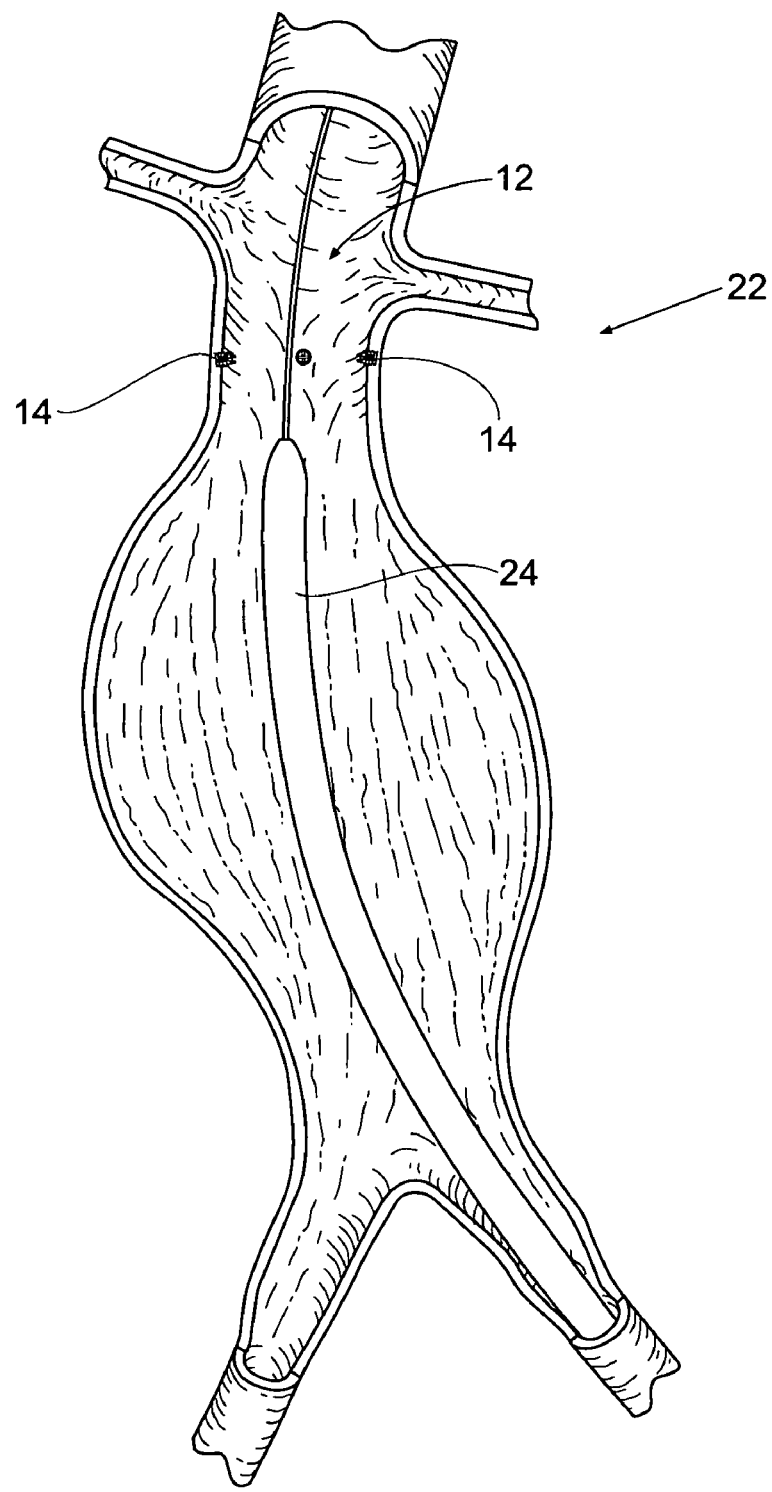

In this arrangement (see FIG. 3), the systems and methods 22 of Type I include a prosthesis delivery catheter 24. The catheter 24 is deployed to the targeted prosthesis attachment site 12, after implantation of the fasteners 14 at the site 12, and after removal of the fastener attachment assembly 10. As FIG. 3 shows, a guide wire helps to guide the catheter 24 to the prosthesis attachment site 12. The catheter 24 carries a prosthesis 20 for deployment at the targeted site 12 (see FIG. 4), e.g., by radial expansion of the prosthesis 20. The prosthesis 20 includes the attachment elements 18. After expansion of the entire prosthesis 20 (or at least the proximal end of the prosthesis 20) (see FIG. 5), the catheter 24 is manipulated to place the attachment elements 18 on the proximal end of the prosthesis 20 into engagement with the attachment elements 16 on the fasteners 14. The prosthesis 20 is thereby anchored in place to the fasteners 14.

The construction and configuration of the fastener attachment assembly 10 and the prosthesis delivery catheter 24 can vary and are not material to the accomplishment of the objectives of systems and methods 22 (or the other systems and methods 40 and 60, to be described later). The fastener attachment assembly 10 can be, e.g., as shown in copending U.S. patent application Ser. No. 10/307,226, filed Nov. 29, 2002, which is incorporated herein by reference. The prosthesis delivery catheter 24 can be of conventional type for delivery of a self-expanding stent graft.

A. The Fastener and its Attachment Elements

The fastener 14 can be variously constructed. For example, the fastener 14 may have various configurations, such as, for example, cylindrical or triangular. The fasteners 14 may be of a metallic fastener staple type (e.g., stainless steel), or may be constructed from a polymeric material.

In one representative embodiment (see FIGS. 6A and 6B), the fastener 14 comprises a helical fastener 24. The helical fastener 24 includes a sharpened distal end 26 and a proximal end 28. The proximal end 28 is preferable sized and configured to limit its penetration into tissue, so that the proximal end 28 is exposed outside tissue in the vessel wall. In the illustrated embodiment, the proximal end 28 includes cap or carrier 74 that comes completely across the diameter. The carrier 74 prevents the fastener 24 from being an open coil and to control the depth of penetration into the tissue. The carrier 74 also includes a slot 76 that enables coupling of the fastener 24 to a suitable drive mechanism, e.g., of a type shown in copending U.S. patent application Ser. No. 10/307,226, filed Nov. 29, 2002, which has been incorporated herein by reference.

Figure 6A:
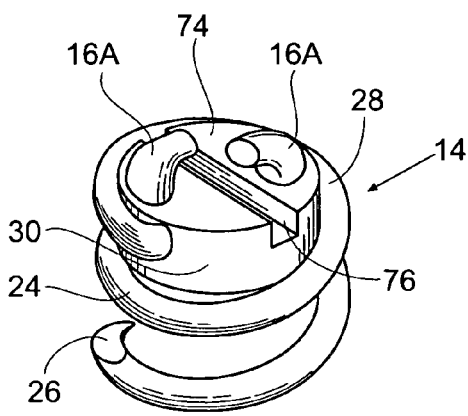
FIGS. 6A to 6E are perspective views of fasteners that can be used with the systems and methods shown in FIGS. 1 to 5, the fasteners having various types of attachment elements.
Figure 6B:
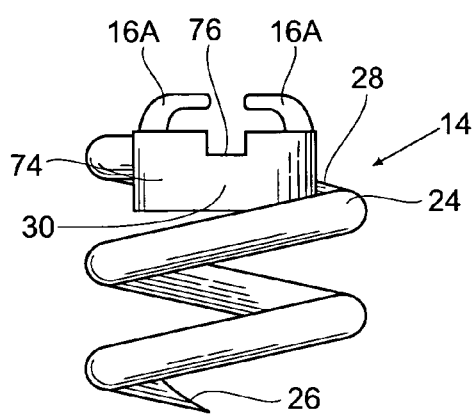
Figure 6C:
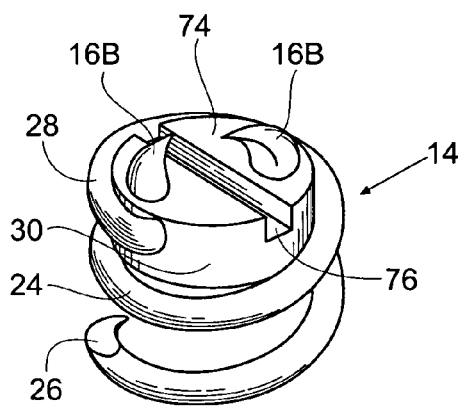
Figure 6D:
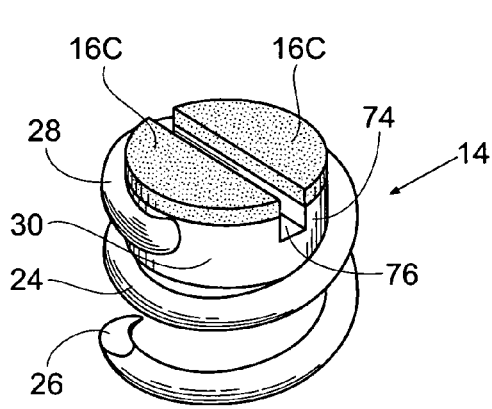
Figure 6E:
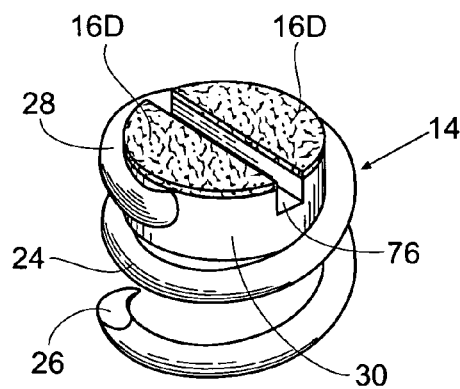

The carrier 74 can be variously sized and configured to include an appropriate attachment element 16. The attachment element 16 can, e.g., comprise a hook 16A (as shown in FIG. 6A); or a barb 16B (see FIG. 6C); or a permanent magnet 16C (see FIG. 6D) ; or a chemical bonding agent 16D (see FIG. 6E). As has been explained, these forms of attachment elements 16 are sized and configured to couple to a compatible attachment element 18 on the prosthesis 20 deployed in the site 12.

The illustrated forms of attachment elements 16 are not exhaustive of the possible sizes and configurations arrangements for the attachment elements 16. If given fastener 14 has means, after the fastener 16 has been implanted, to accommodate the fastening of a later-deployed prosthesis 20, the fastener 14 can be defined as having an attachment element 16. Likewise, different styles of attachment elements 16 can be used in conjunction with one another, provided attachment between the prosthesis 20 and the fastener 14 occurs. For instance, hooks and barbs may be used together.

Desirably, the fastener 14 and/or attachment element 16 includes a radio-opaque marker material 30. The material 30 aids the visualization of the fastener/attachment element 14/16 for alignment with and attachment to the prosthesis 20.

B. The Prosthesis and its Attachment Elements

Figure 4:
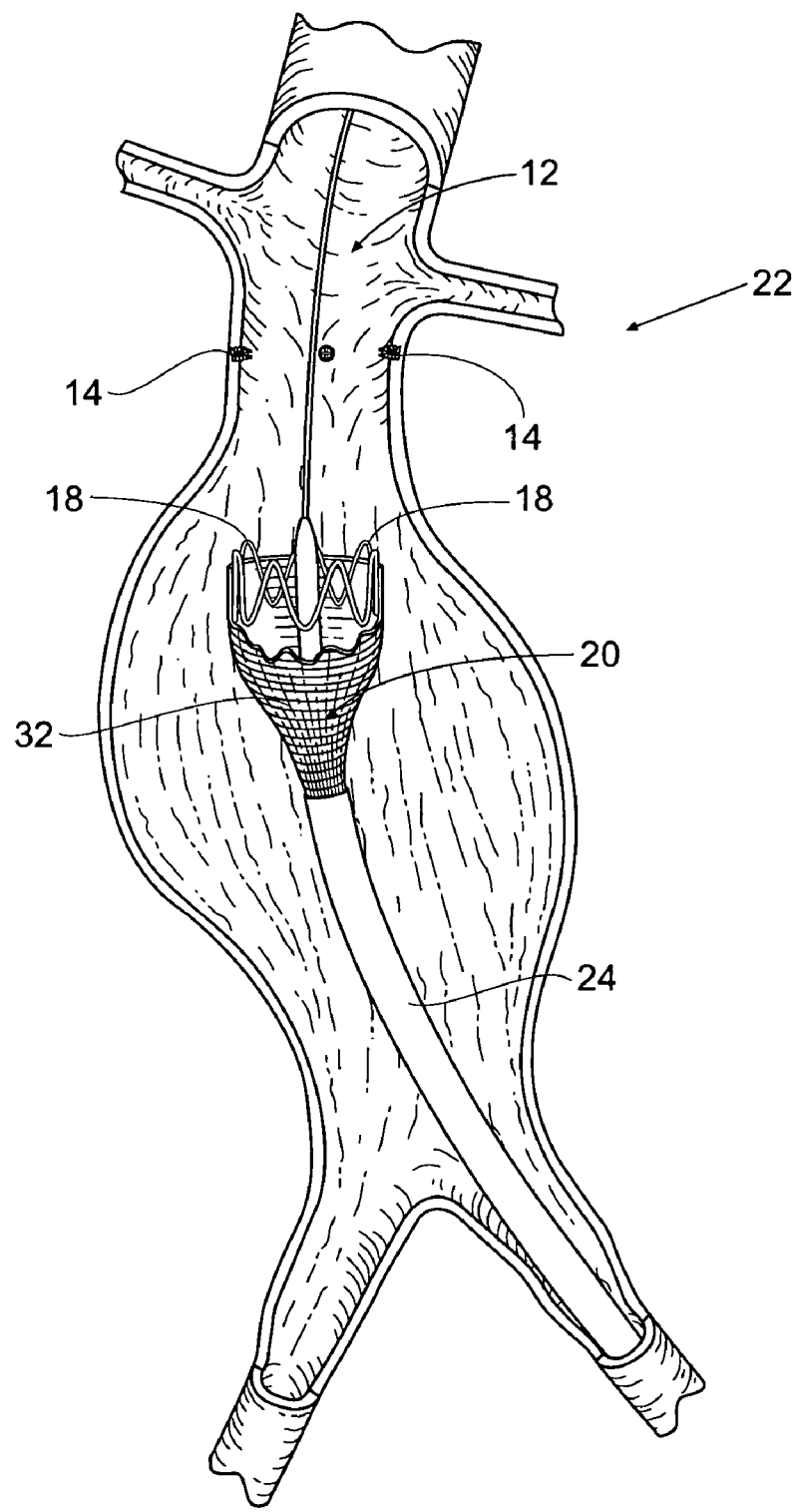
Figure 5:
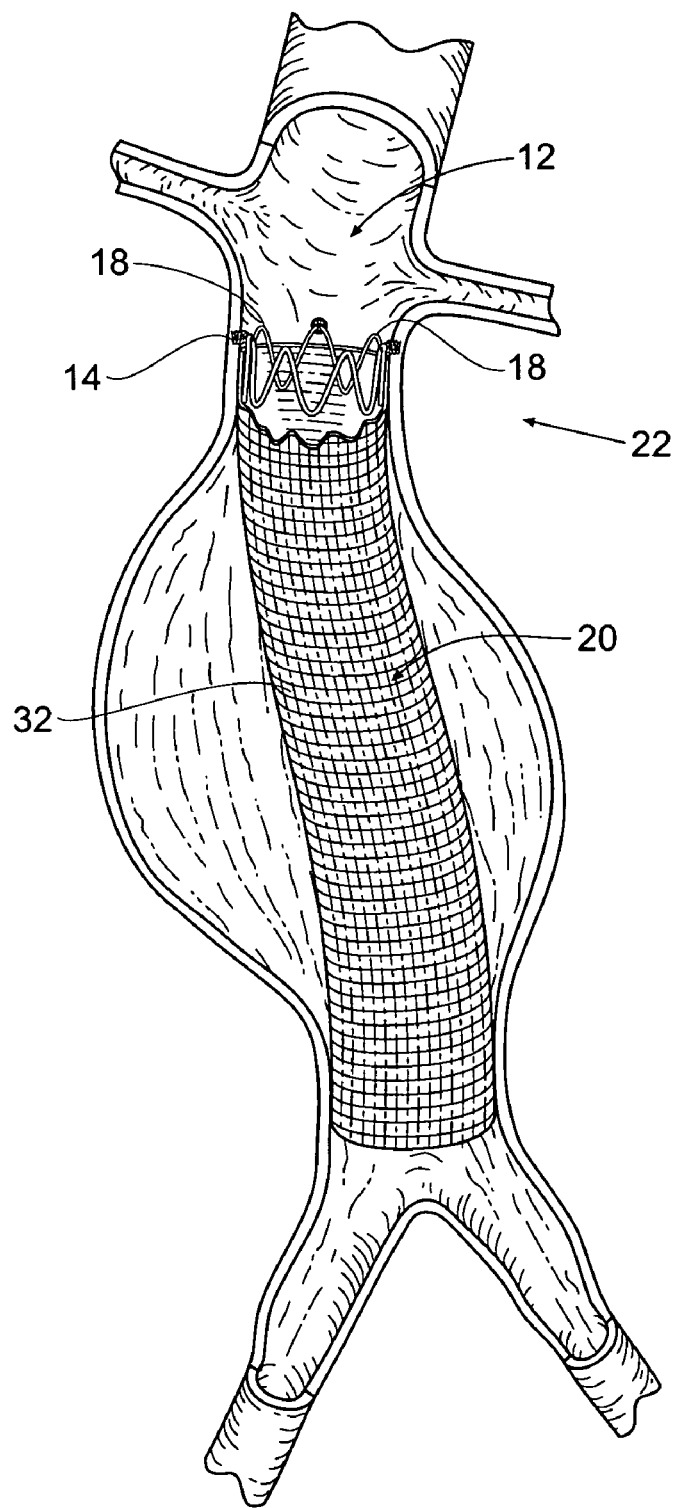

The prosthesis 20 (see FIGS. 7A and 7B) desirably incorporates a support frame or scaffold 32. The scaffold 32 may be elastic, e.g., comprised of a shape memory alloy elastic stainless steel, or the like. For elastic scaffolds, expanding typically comprises releasing the scaffolding from a constraint to permit the scaffold to self-expand at the implantation site. A sheath carried by the prosthesis delivery catheter 24 covers and constrains the scaffold 32 in a radially compressed condition during while the catheter 24 is steered to the targeted site 12. In this arrangement, self-expansion of the scaffold 32 is achieved by pulling back on the sheath (as FIG. 4 shows), to permit the scaffold 32 to radially expand and assume its larger diameter configuration.

Alternatively, the scaffold 32 may be constrained in an axially elongated configuration, e.g., by attaching either end of the scaffold to an internal tube, rod, catheter or the like. This maintains the scaffold 32 in the elongated, reduced diameter configuration. The scaffold 32 may then be released from such axial constraint in order to permit self-expansion.

Alternatively, the scaffold 32 may be formed from a malleable material, such as malleable stainless steel of other metals. Expansion may-then comprise applying a radially expansive force within the scaffold 32 to cause expansion, e.g., inflating a scaffold delivery catheter within the scaffold in order to affect the expansion. In this arrangement, the positioning and deployment of the endograft can be accomplished by the use of an expansion means either separate or incorporated into the deployment catheter 24. This will allow the prosthesis 20 to be positioned within the vessel and partially deployed while checking relative position within the vessel. The expansion can be accomplished either via a balloon or mechanical expansion device. Additionally, this expansion stabilizes the position of the prosthesis 20 within the artery by resisting the force of blood on the endograft until the prosthesis can be fully deployed.

The prosthesis 20 may have a wide variety of conventional configurations. It can typically comprise a fabric or some other blood semi-impermeable flexible barrier which is supported by the scaffold 32, which can take the form of a stent structure. The stent structure can have any conventional stent configuration, such as zigzag, serpentine, expanding diamond, or combinations thereof. The stent structure may extend the entire length of the graft, and in some instances can be longer than the fabric components of the graft. Alternatively, the stent structure can cover only a small portion of the prosthesis, e.g., being present at the ends. The stent structure may have three or more ends when it is configured to treat bifurcated vascular regions, such as the treatment of abdominal aortic aneurysms, when the stent graft extends into the iliac arteries. In certain instances, the stent structures can be spaced apart along the entire length, or at least a major portion of the entire length, of the stent-graft, where individual stent structures are not connected to each other directly, but rather connected to the fabric or other flexible component of the graft.

Figure 7A:
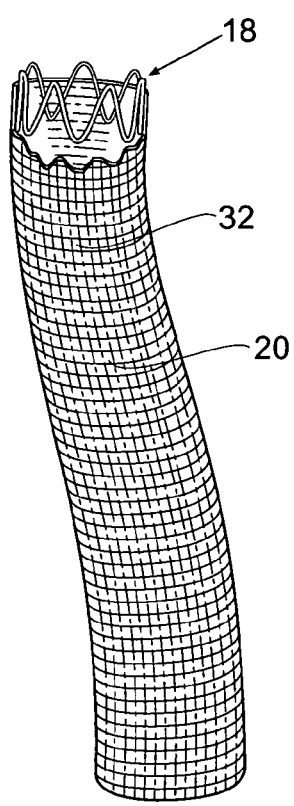
FIGS. 7A and 7B are views of prostheses that can be used with the systems and methods shown in FIGS. 1 to 5, the prostheses having attachment elements that couple to attachment elements carried by fasteners of the type shown in FIGS. 6A to 6E.
Figure 7B:
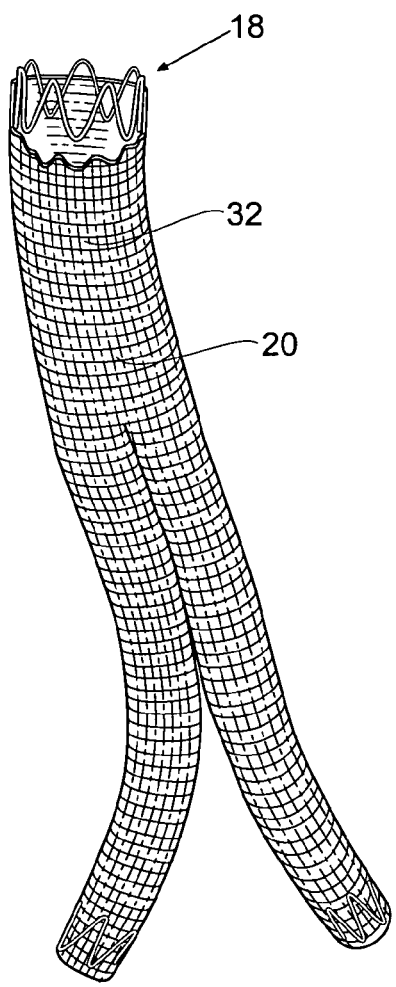

The prosthesis 20 can be sized and figured to be either straight or bifurcated form. FIG. 7A shows a straight prosthesis 20. FIG. 7B shows a bifurcated prosthesis 20.

As previously described, the prosthesis 20 includes the attachment elements 18 that couple in a compatible fashion to the attachment elements 16 on the fasteners 14. The size and configuration of the prosthesis attachment elements 18 are selected to be compatible with the size and configuration of fastener attachment elements 18, to enable coupling the attachment elements 16 and 18 together.

Figure 8A:
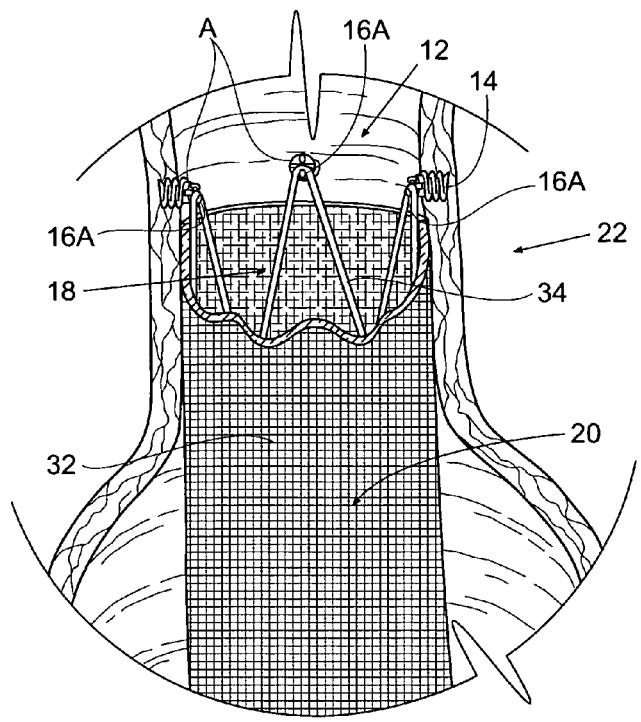
FIGS. 8A and 8B show a prosthesis that has been mechanically coupled to fasteners implanted in a vessel wall or hollow body organ, which is illustrative of one embodiment of the systems and methods of the type shown in FIGS. 1 to 5.
Figure 8B:
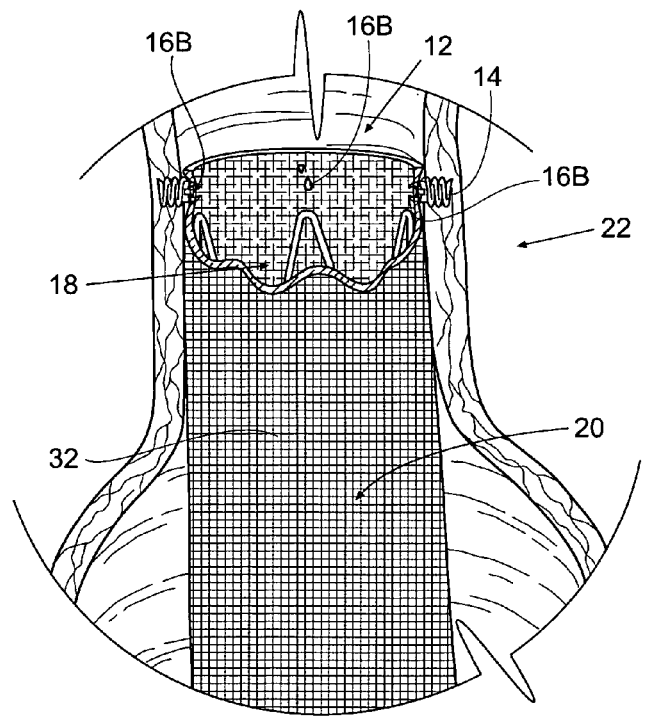
Figure 9:
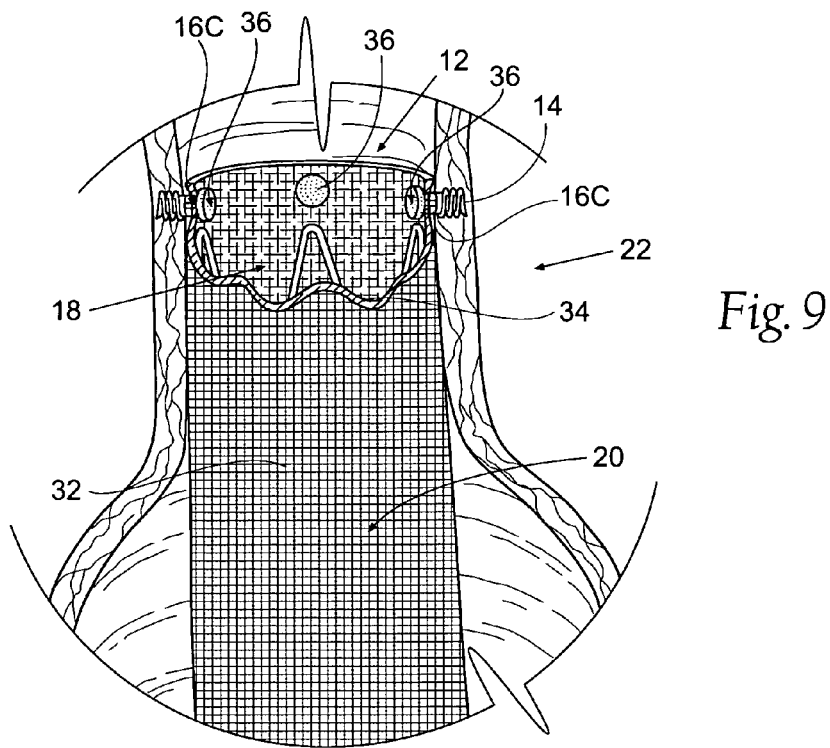
FIG. 9 shows a prosthesis that has been magnetically coupled to fasteners implanted in a vessel wall or hollow body organ, which is illustrative of another embodiment of the systems and methods of the type shown in FIGS. 1 to 5.
Figure 10:
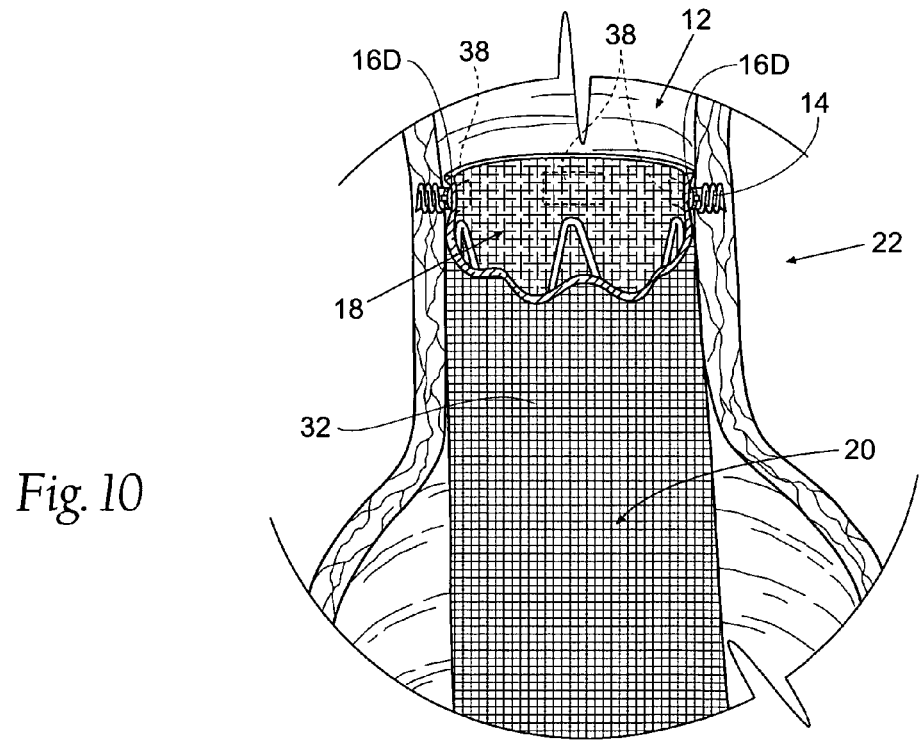
FIG. 10 shows a prosthesis that has been chemically coupled to fasteners implanted in a vessel wall or hollow body organ, which is illustrative of another embodiment of the systems and methods of the type shown in FIGS. 1 to 5.

For example (see FIG. 8A), when the fastener attachment elements 16 comprise a mechanical coupling arrangement (e.g., the hooks 16A in FIG. 6C), the compatible attachment element 18 on the prosthesis 20 can comprise a proximal stent structure 34, which mechanically engages the attachment elements 16 to couple the fasteners 14 to the prosthesis 20. As FIG. 8B shows, when the mechanical coupling arrangement comprises the barbs 16B in FIG. 6C, the compatible attachment element 18 on the prosthesis 20 can comprise a zone in the prosthesis 20, which the barbs 16B can penetrate to couple the fasteners 14 to the prosthesis 20.

Alternatively (see FIG. 9), when the fastener attachment elements 16 comprise magnetic coupling arrangements (e.g., the magnet 16C in FIG. 6D), the compatible attachment elements 18 on the prosthesis 20 can comprise magnets 36 carried on the proximal end of the prosthesis 20. The magnets 36 have an opposite magnetic orientation than the fastener magnets 16C or otherwise comprise a ferromagnetic material that is attracted to the fastener magnet 16C to thereby magnetically engage the attachment elements 16 to couple the fasteners 14 to the prosthesis 20.

Alternatively (see FIG. 10), when the fastener attachment elements 16 comprise chemical coupling arrangements (e.g., the chemical material 16D in FIG. 6E), the compatible attachment element 18 on the prosthesis 20 can comprise a compatible material 38 carried on the proximal end of the prosthesis 20. The compatible material 38 adheres or bonds to the chemical material 16D, to thereby chemically engage the attachment elements 16 to couple the fasteners 14 to the prosthesis 20.

The Type I arrangement makes possible the precise placement of fasteners in a desired location within a vessel or hollow body organ in preparation for deployment of a prosthesis. The fasteners serve as positional markers for the precise deployment of the prosthesis in the vessel or hollow body organ. The fasteners also provide a secure, permanent attachment of the prosthesis in the vessel or hollow body organ.

II. Type II Systems and Methods

Figure 11:
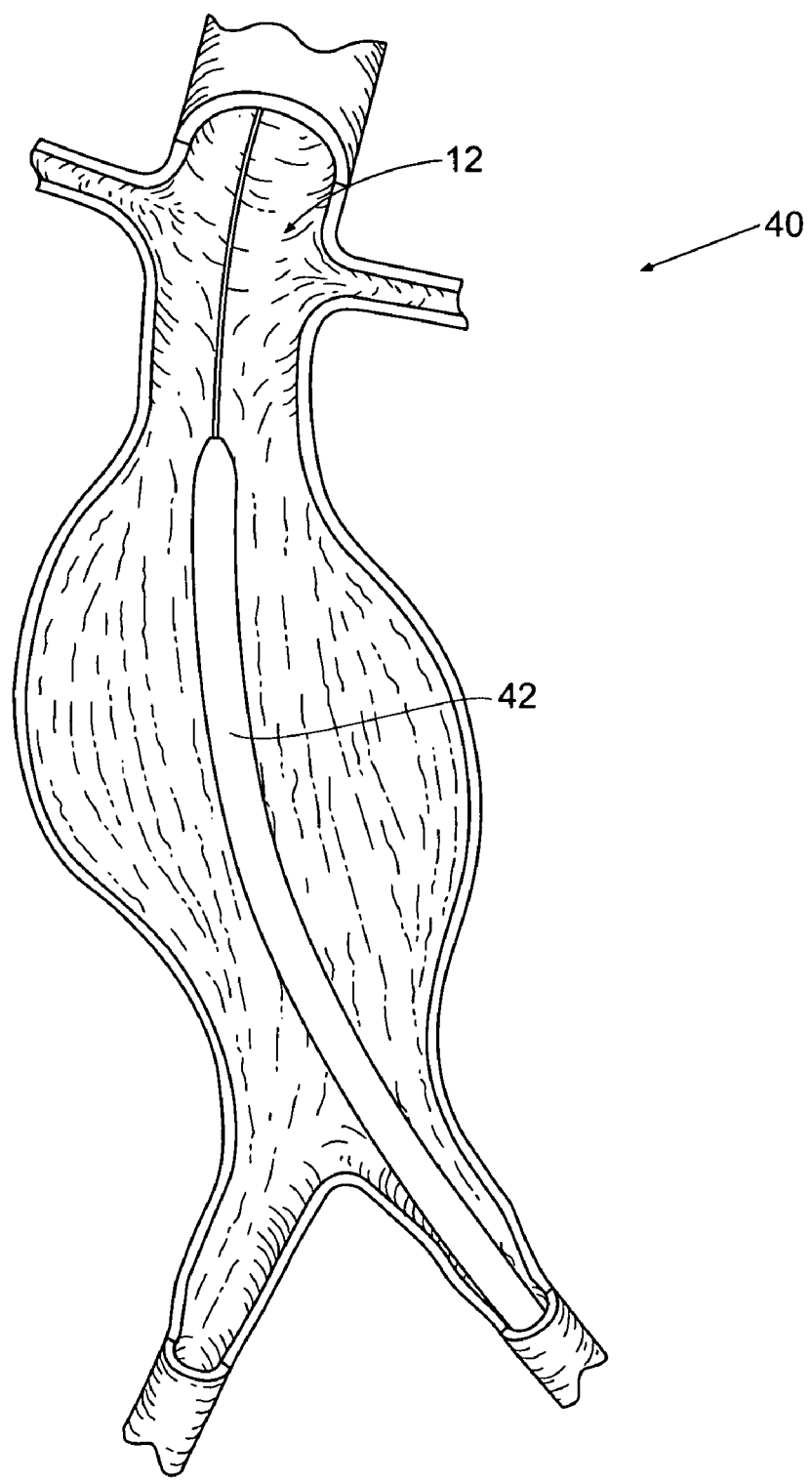
FIGS. 11 to 15 show another type of a system and method for attaching a prosthesis to a vessel wall or hollow body organ, in which the prosthesis is coupled to a stent ring, which has been implanted prior to deployment of the prosthesis.

FIGS. 11 to 21 depict the systems and methods 40 that can be characterized as a Type II arrangement. In this embodiment, the systems and methods 40 include a stent ring 44 that is implanted by a stent ring attachment assembly 42 prior to deployment of a prosthesis 50. As shown in FIG. 11, the assembly 42 is deployed to a targeted prosthesis attachment site 12, which, like FIG. 1, is shown as being within an abdominal aortic aneurysm. FIG. 11 shows the attachment assembly 42 being deployed over a guide wire.

Figure 12:
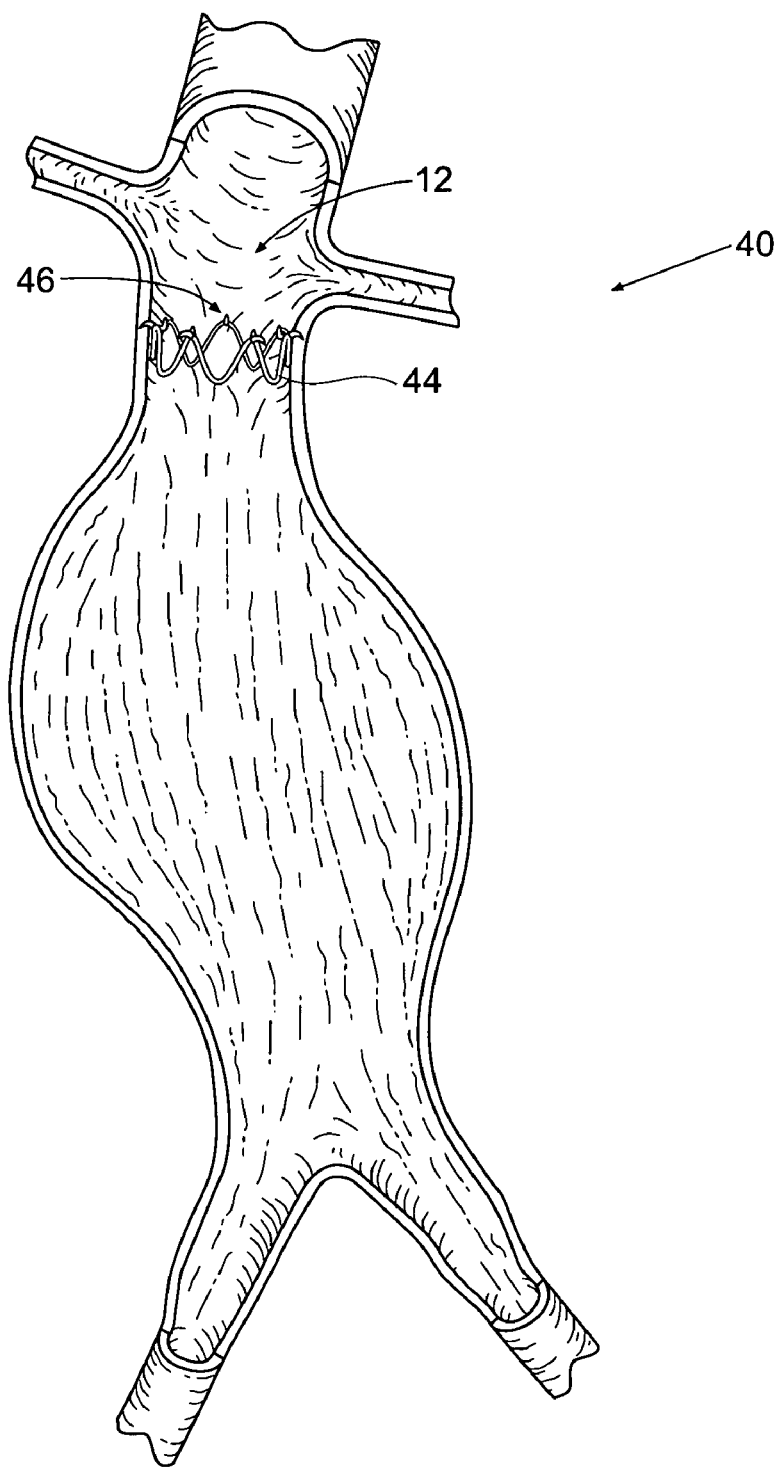

As FIG. 12 shows, the stent ring attachment assembly 42 serves the function of implanted one or more stent rings 44 in the vessel wall at the targeted site 12. As will be described in greater detail, the stent rings 44 each includes an attachment element 46 that, in use, couples to a corresponding attachment element 48 on a prosthesis 50 deployed in the site 12.

Figure 13:
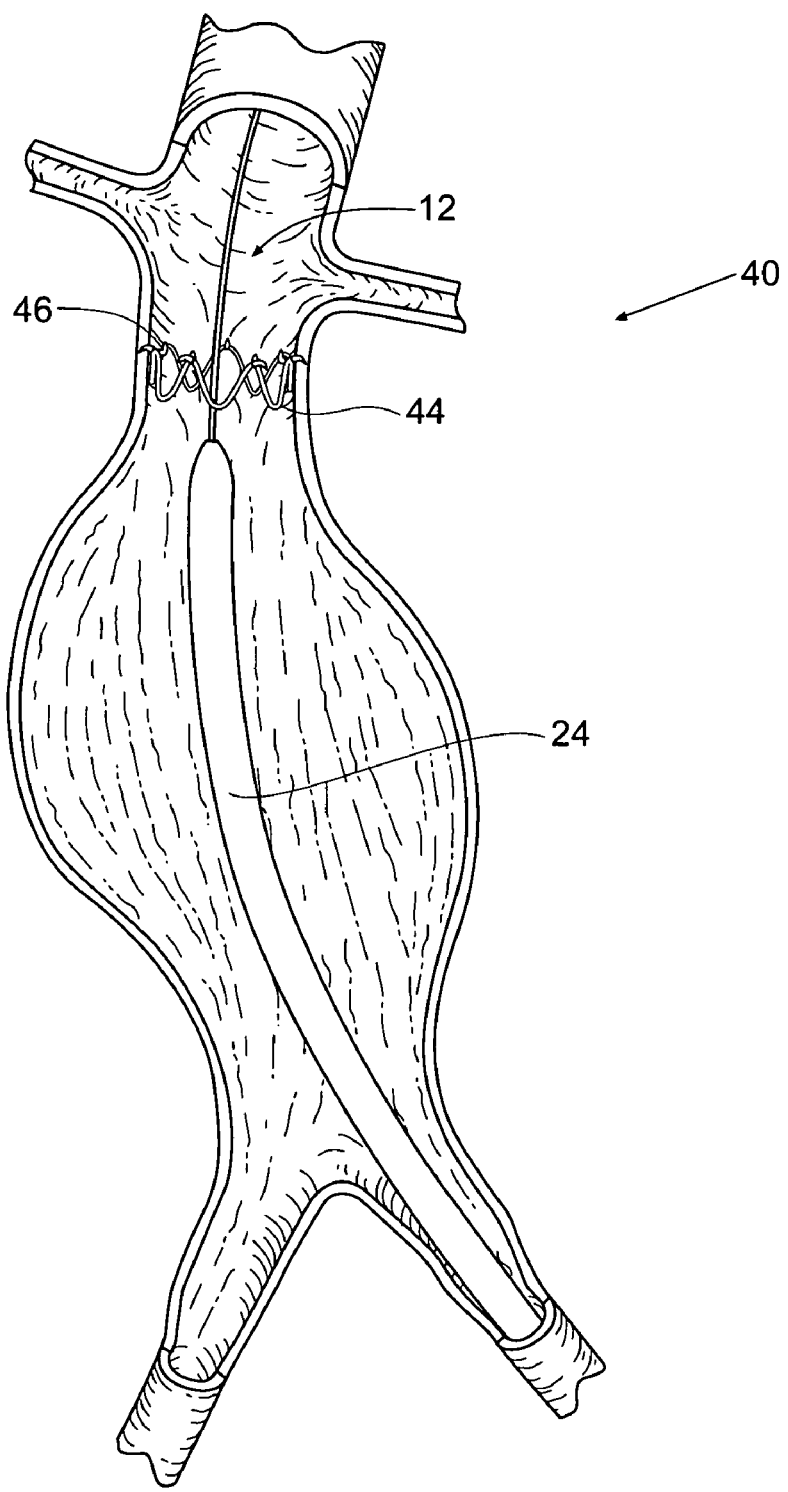
Figure 14:
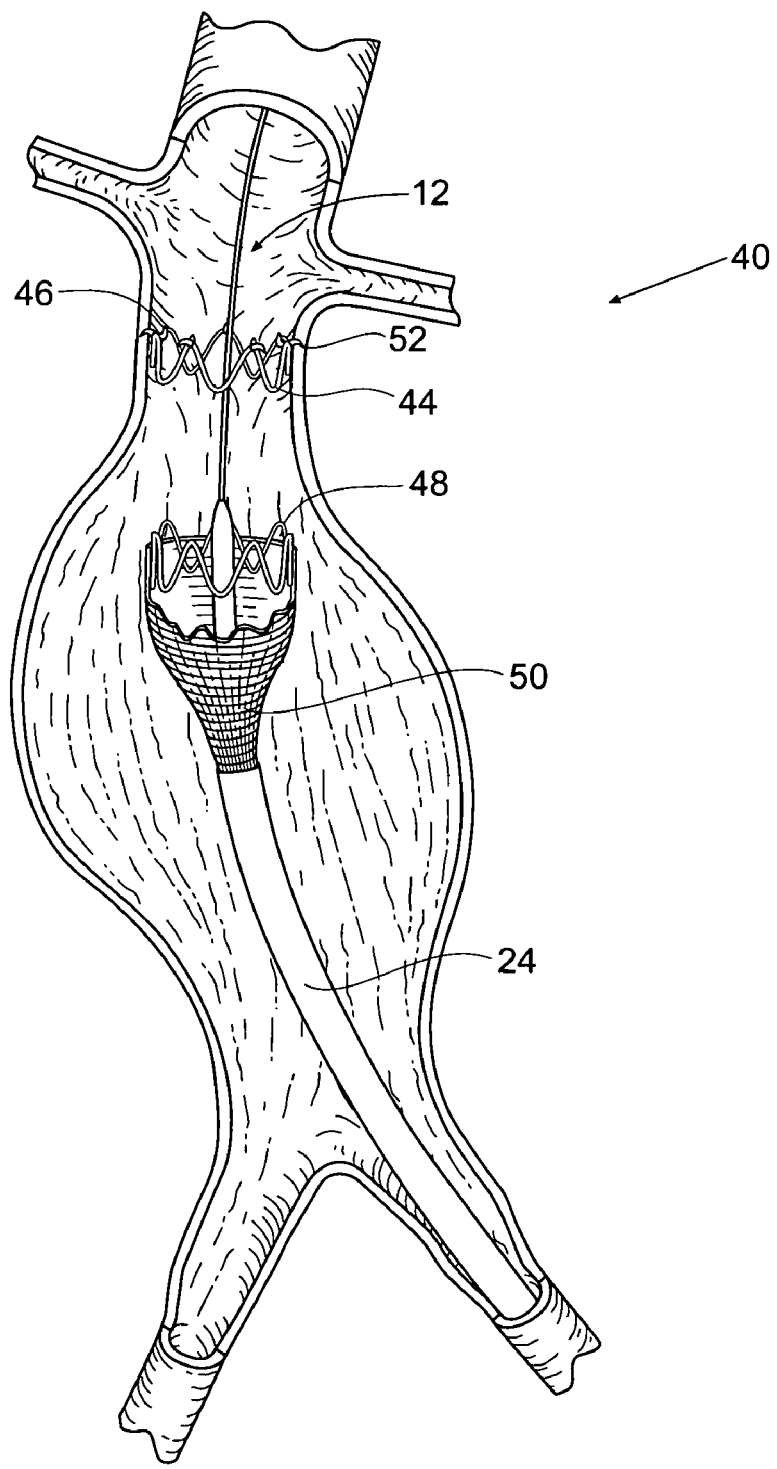

In this arrangement (see FIG. 13), the systems and methods 40 of Type II include a prosthesis delivery catheter 24, like the one previously described in the Type I arrangement. The catheter 24 is deployed to the targeted prosthesis attachment site 12, after implantation of the stent ring 44 or rings at the site 12, and after removal of the stent ring attachment assembly 42. FIG. 13 shows the catheter 24 being deployed over a guide wire.

The catheter 24 carries a prosthesis 50 for deployment at the targeted site 12 (see FIG. 14), e.g., by radial expansion of the prosthesis 50. The prosthesis 20 includes the attachment elements 48. After expansion of the prosthesis 50 (or at least the proximal end of the prosthesis 50) (see FIG. 15), the catheter 24 is manipulated to move the attachment elements 48 on the prosthesis 50 into engagement with the attachment elements 46 on the stent ring 44. The prosthesis 50 is thereby anchored in place by the stent ring 44.

A. The Stent Ring and its Attachment Elements

The stent ring 44 (see FIG. 16) can be variously constructed. The stent ring 44 may be elastic, e.g., comprised of a shape memory alloy elastic stainless steel, or the like. For elastic stent rings 44, expanding typically comprises releasing the stent ring 44 from a constraint to permit the stent ring 44 to self-expand at the implantation site. For example, a sheath carried by the stent ring attachment assembly 42 covers and constrains the stent ring 44 in a radially compressed condition during while the assembly 42 is steered to the targeted site 12. In this arrangement, self-expansion of the stent ring 44 is achieved by pulling back on the sheath, to permit the stent ring 44 to radially expand and assume its larger diameter configuration.

Alternatively, the stent ring 44 may be formed from a malleable material, such as malleable stainless steel of other metals. Expansion may then comprise applying a radially expansive force within the stent ring 44 to cause expansion, e.g., inflating a delivery catheter within the stent ring 44 in order to affect the expansion. In this arrangement, the positioning and deployment of the prosthesis 50 can be accomplished by the use of an expansion means either separate or incorporated into the stent ring attachment assembly 42. The expansion can be accomplished either via a balloon or mechanical expansion device. Additionally, this expansion stabilizes the position of the prosthesis 50 within the artery by resisting the force of blood on the endograft until the prosthesis can be fully deployed.

Figures 15, 16:
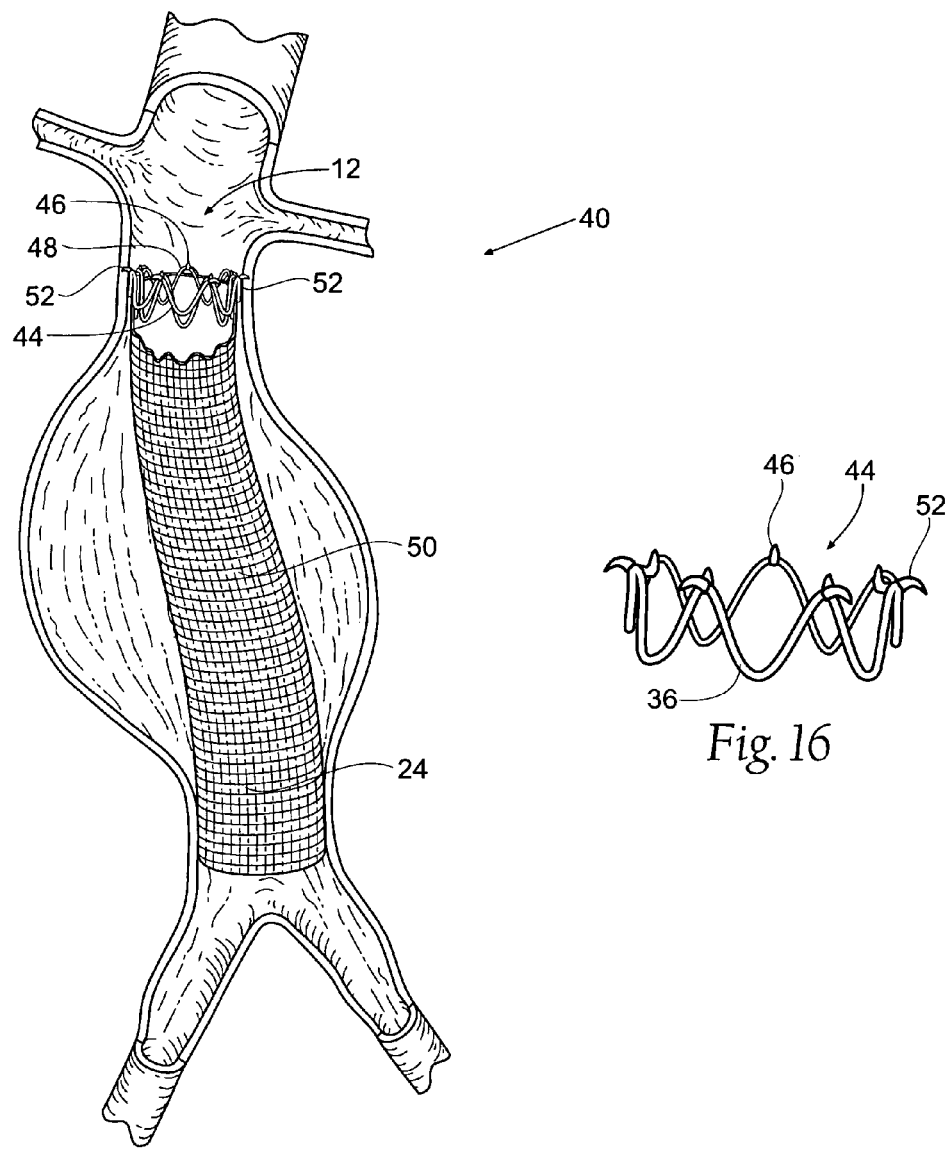
FIG. 16 is a perspective view of a stent ring that can be used in association with the systems and methods shown in FIGS. 11 to 15.

The stent ring 44 includes an element 52 to secure the stent ring 44 to a vessel or body organ. The element 52 can take various forms, e.g., hooks or barbs, or a supra-renal stent, and/or combinations thereof. In FIG. 16, the element 52 comprises barbs, which engage and anchor into tissue upon expansion of the ring stent 44.

Figure 17A:
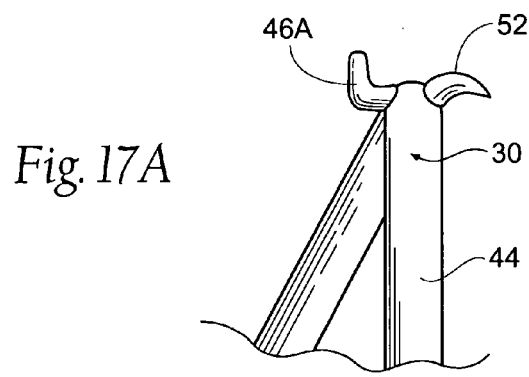
FIGS. 17A to 17D are perspective views of various types of attachment elements that the stent ring shown in FIG. 16 can employ to accommodate coupling to a prosthesis.
Figure 17B:
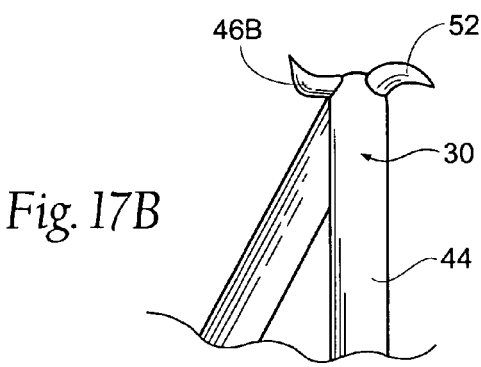
Figure 17C:
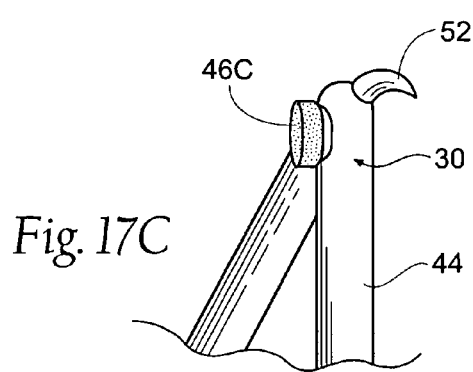
Figure 17D:
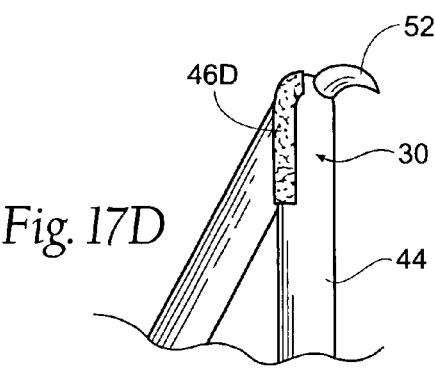

In this arrangement, the stent ring 44 includes an appropriate attachment element 46. As shown in FIGS. 17A to 17D, the attachment element 46 can take similar form as the fastener attachment elements 16 previously described, e.g., a hook 46A (as shown in FIG. 17A); or a barb 46B (see FIG. 17B); or a permanent magnet 46C (see FIG. 17C); or a chemical bonding agent 46D (see FIG. 17D). As has been explained, these forms of attachment elements 46 are sized and configured to couple to a compatible attachment element 48 on the prosthesis 50 deployed in the site 12.

The illustrated forms of attachment elements 46 are not exhaustive of the possible sizes and configurations arrangements for the attachment elements 46. If given ring stent 44 has means, after the ring stent 44 has been deployed, to accommodate the fastening of a later-deployed prosthesis 50, the ring stent 44 can be defined as having an attachment element 46. Likewise, different styles of attachment elements 46 can be used in conjunction with one another, provided attachment between the prosthesis 50 and the fastener 14 occurs. For instance, hooks and barbs may be used together.

Desirably, the ring stent 44 and/or attachment elements 46 includes a radio-opaque marker material 30. The material 30 aids the visualization of the ring stent 44/attachment element 46 for alignment with and attachment of the prosthesis 50.

B. The Prosthesis and its Attachment Elements

Figure 18:
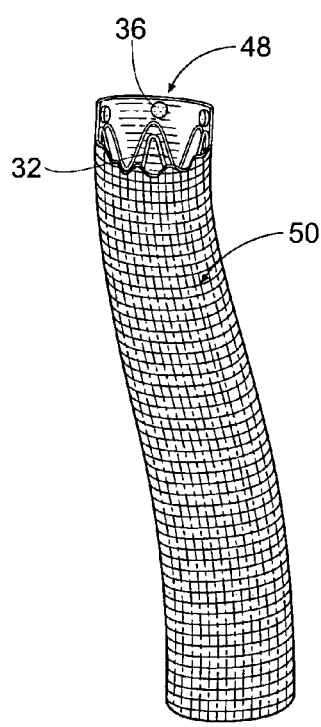
FIG. 18 is a view of a prosthesis that can be used with the systems and methods shown in FIGS. 11 to 15, the prostheses having attachment elements that couple to attachment elements carried by a stent ring of the type shown in FIGS. 17A to 17D.
Figure 23:
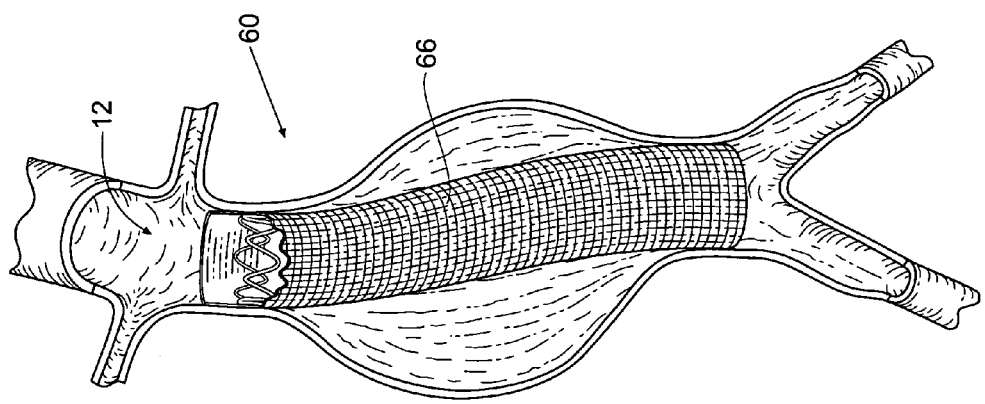
FIGS. 22 to 25 show another type of a system and method for attaching a prosthesis to a vessel wall or hollow body organ, in which a stent ring is fastened to a prosthesis, which has been deployed prior to implantation of the stent ring.

The prosthesis 50 (see FIG. 18) can share the same attributes of the prosthesis 20. It desirably incorporates a support frame or scaffold 32, as previously described and be deployed in the same manner. Like the prosthesis 20, the prosthesis 50 may have a wide variety of conventional configurations. It can be sized and figured to be either straight or bifurcated form. FIG. 18 shows a straight prosthesis 50 for the purpose of illustration.

As previously described, the prosthesis 50 includes the attachment elements 48 that couple in a compatible fashion to the attachment elements 46 on the stent ring 44. As before explained, the size and configuration of the prosthesis attachment elements 48 are selected to be compatible with the size and configuration of stent ring attachment elements 46, to enable coupling the attachment elements 46 and 48 together. In FIG. 18, the attachment elements 48 take the form of magnets 36, as are also shown in FIG. 20 and which will be described in greater detail later.

For example (see FIG. 19), when the stent ring attachment elements 46 comprise mechanical coupling arrangements (e.g., the barbs 46B shown in FIG. 17B) the compatible attachment element 48 on the prosthesis 50 can comprise a zone in the prosthesis 20, which the barbs 46B can penetrate to couple the couple the stent ring 44 to the prosthesis 50. As another example of a mechanical coupling arrangement (as shown in FIG. 15), when the stent ring attachment elements 46 comprise the hooks 46A (shown in FIG. 17A), the compatible attachment element 48 on the prosthesis 50 can comprise a proximal stent structure 34, which mechanically engages the attachment elements 46 on the stent ring 44 to couple prosthesis 50 to the stent ring 44.

Alternatively (see FIG. 20), when the stent ring attachment elements 46 comprise magnetic coupling arrangements (e.g., the magnet 46C in FIG. 17C), the compatible attachment element 48 on the prosthesis 50 can comprise a magnet 36 carried on the proximal end of the prosthesis 50 having an opposite magnetic orientation or which has a ferromagnetic material that is otherwise attracted to the stent ring magnet 46C to thereby magnetically engage the stent ring attachment elements 46 and couple the stent ring 44 to the prosthesis 50.

Alternatively (see FIG. 21), when the fastener attachment elements 46 comprise chemical coupling arrangements (e.g., the chemical material 46D in FIG. 17D), the compatible attachment element 48 on the prosthesis 50 can comprise a compatible material 38 on the proximal end of the prosthesis 50 that bonds to the chemical material 46D, to thereby chemically engage the attachment elements 46 and couple the stent ring 44 to the prosthesis 50.

It can be seen that the attachment mechanisms between the fasteners 14 and prosthesis 20 in the Type I arrangement and the attachment mechanisms between the stent ring 44 and prosthesis 50 in the Type II arrangement are functionally similar.

The Type II arrangement makes possible the precise placement of a stent ring in a desired location within a vessel or hollow body organ in preparation for deployment of a prosthesis. The stent ring serves as positional marker for the precise deployment of the prosthesis in the vessel or hollow body organ. The stent ring also provides a secure, permanent attachment of the prosthesis in the vessel or hollow body organ.

III. Type III Systems and Methods

Figure 22:
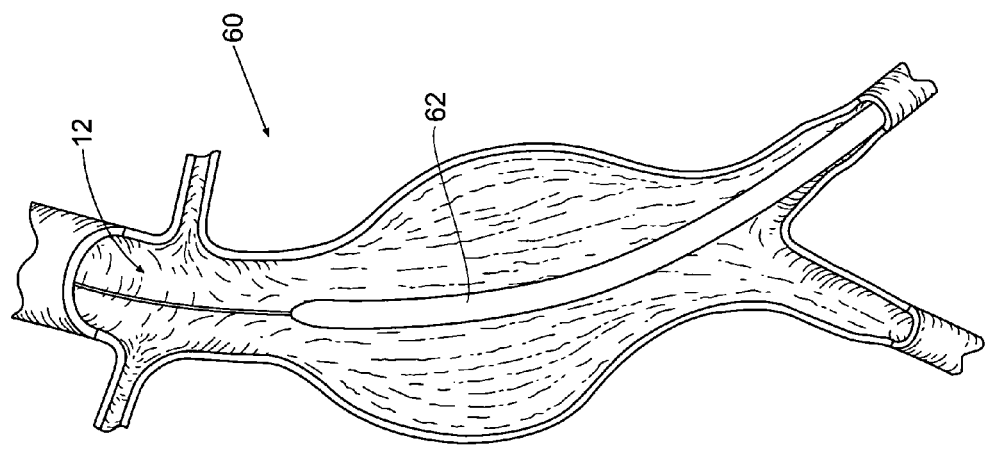

FIGS. 22 to 25 depict the systems and methods 60 that can be characterized as a Type III arrangement. In this embodiment, the systems and methods 60 include a prosthesis delivery catheter 62 (see FIG. 22), like the ones previously described with respect to the Type I and II arrangements. As FIG. 22 shows, the catheter 62 is deployed to the targeted prosthesis attachment site 12, which, like FIGS. 3 and 13, is shown as being within an abdominal aortic aneurysm. FIG. 22 shows the catheter 62 being deployed over a guide wire.

Unlike the systems and methods 40 of the Types I and II arrangements, the prosthesis delivery catheter 62 of the Type III arrangement is deployed before implantation of fasteners 14 or a stent ring 64 at the site 12. The catheter 62 carries a prosthesis 66 for deployment at the targeted site 12 (see FIG. 23), e.g., by radial expansion of the prosthesis 66, as previously described.

Figure 24:
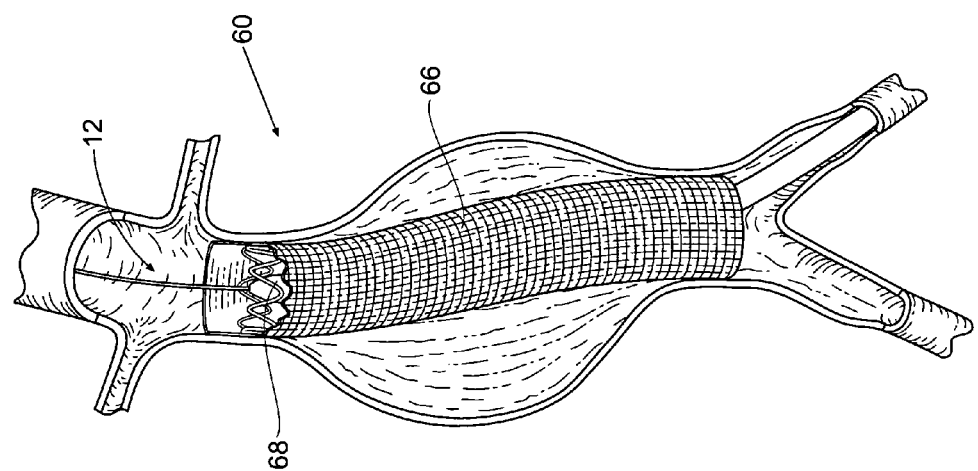

The systems and methods 60 of Type III include a stent ring attachment assembly 68. As shown in FIG. 24, in the Type III arrangement, the stent ring attachment assembly 68 is deployed within the prosthesis 66 after deployment of the prosthesis 66 and after the prosthesis delivery catheter 62 has been withdrawn.

Figure 25:
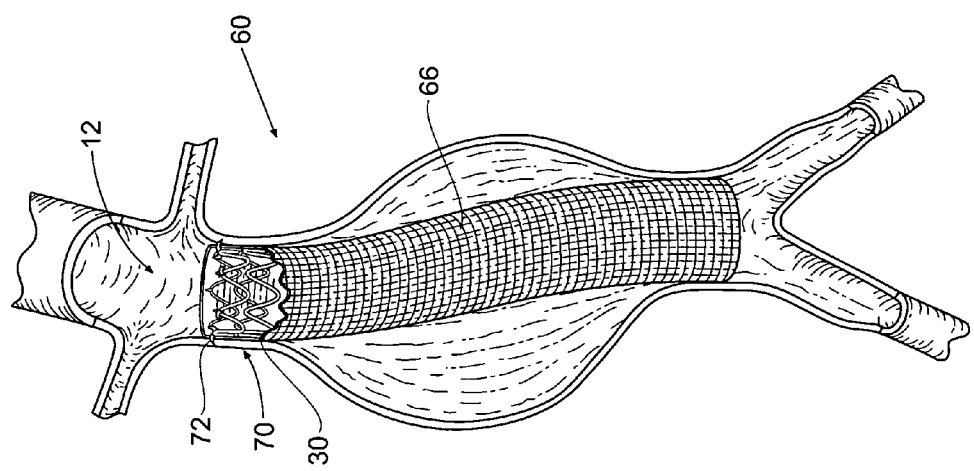

As FIG. 25 shows, the stent ring attachment assembly 68 serves the function of implanted one or more stent rings 70 in the vessel wall at the targeted site 12. The stent ring 70 includes elements 72 to pass through the proximal end of the prosthesis 66 and secure the stent ring 70 to a vessel or body organ. The elements 72 can take various forms, e.g., hooks or barbs, or a supra-renal stent, and/or combinations thereof, as previously described in connection with the Type II arrangement. The prosthesis 66 is thereby anchored in place by the stent ring 44.

As before described, the stent ring 70 and/or locations on the prosthesis 66 desirable includes a radio-opaque marker material 30. The material 30 aids the visualization of the stent ring 70 and/or prosthesis 66 for alignment with and attachment of the prosthesis 50.

The Type III arrangement enables the implantation of an anchoring device (i.e., the stent ring) all at once after a prosthesis has been deployed.

The embodiments of the invention are described above in detail for the purpose of setting forth a complete disclosure and for the sake of explanation and clarity. Those skilled in the art will envision other modifications within the scope and sprit of the present disclosure.

I claim:

1. A method for securing a prosthesis to tissue in a targeted tissue region comprising:
   (i) providing at least one helical fastener including a sharpened distal body region configured for penetrating tissue in response to a rotational implantation force and a proximal body region having a diameter, a carrier on the proximal body region that extends completely across the diameter to limit penetration of the proximal body region into tissue, the carrier including an attachment element that, when the distal body region is in a tissue penetrating condition, is exposed outside tissue to mark a targeted prosthesis placement site in advance of deployment of a prosthesis;
   (ii) providing a prosthesis including an attachment element configured, in response to manipulation of the prosthesis relative to the attachment element of the carrier, to mechanically engage the attachment element of the carrier;
   (iii) introducing the at least one fastener into the targeted tissue region;
   (iv) implanting the fastener in tissue in the targeted tissue region including coupling an actuator to the carrier for imparting the rotational implantation force to the fastener to place the distal body region in the tissue penetrating condition exposing the attachment element of the carrier outside tissue to mark the targeted prosthesis placement site;
   (v) after (iii) and (iv), introducing the prosthesis into the targeted tissue region including introducing a prosthesis delivery catheter to deploy the prosthesis at the targeted prosthesis placement site marked by the attachment element of the carrier, and
   (vii) manipulating the prosthesis to mechanically engage the attachment element of the prosthesis with the attachment element of the carrier to thereby couple the prosthesis to the fastener to secure the prosthesis to tissue at the targeted prosthesis placement site.

2. A method according to claim 1 wherein the attachment element of the carrier and the attachment element of prosthesis comprise a cooperating mechanical coupling assembly.

3. A method according to claim 2 wherein the mechanical coupling assembly includes a hook.

4. A method according to claim 2 wherein the cooperating mechanical coupling assembly includes a barb.

5. A method according to claim 1 wherein the cooperating attachment elements includes a magnetic coupling assembly.

6. A method according to claim 1 wherein the cooperating attachment elements includes a chemical coupling assembly.

7. A method according to claim 1 wherein the attachment element of the carrier includes a radio-opaque marker material to mark the targeted prosthesis placement site.

* * * * *